10,614,568 B2

United States Patent
Noji et al.

(10) Patent No.: US 10,614,568 B2
(45) Date of Patent: Apr. 7, 2020

(54) DYNAMIC ANALYSIS SYSTEM

(71) Applicant: Konica Minolta, Inc., Tokyo (JP)

(72) Inventors: Sho Noji, Kokubunji (JP); Koichi Fujiwara, Osaka (JP); Hitoshi Futamura, Hachioji (JP); Akinori Tsunomori, Kodaira (JP)

(73) Assignee: KONICA MINOLTA, INC., Tokyo (JP)

( * ) Notice: Subject to any disclaimer, the term of this patent is extended or adjusted under 35 U.S.C. 154(b) by 121 days.

(21) Appl. No.: 15/448,814

(22) Filed: Mar. 3, 2017

(65) Prior Publication Data

US 2017/0278238 A1 Sep. 28, 2017

(30) Foreign Application Priority Data

Mar. 28, 2016 (JP) ................................. 2016-063125

(51) Int. Cl.
G06T 7/00 (2017.01)
A61B 6/00 (2006.01)

(52) U.S. Cl.
CPC ............ *G06T 7/0012* (2013.01); *A61B 6/486* (2013.01); *A61B 6/50* (2013.01); *A61B 6/504* (2013.01); *A61B 6/5217* (2013.01); *G06T 2207/10116* (2013.01); *G06T 2207/30061* (2013.01)

(58) Field of Classification Search
CPC ..................... G06T 7/0012; G06T 2207/30061
See application file for complete search history.

(56) References Cited

U.S. PATENT DOCUMENTS

| 2004/0092811 | A1* | 5/2004 | Hill ........................ A61B 6/032 600/413 |
| 2005/0025365 | A1* | 2/2005 | Oosawa ................ G06T 7/0012 382/218 |
| 2005/0147285 | A1* | 7/2005 | Tago ........................ G06T 7/254 382/130 |
| 2006/0239530 | A1* | 10/2006 | Oosawa ................ G06T 7/0012 382/130 |
| 2010/0246925 | A1* | 9/2010 | Nagatsuka ............... A61B 5/08 382/132 |

(Continued)

FOREIGN PATENT DOCUMENTS

| JP | 2009-519082 A | 5/2009 |
| JP | 2009-148336 A | 7/2009 |

(Continued)

OTHER PUBLICATIONS

Naini et al., "Estimation of Lung's Air Volume and Its Variations Throughout Respiratory CT Image Sequences", IEEE Transactions on Biomedical Engineering, vol. 58 No. 1, Jan. 2011, pp. 152-158 (Year: 2011).*

(Continued)

*Primary Examiner* — Nay A Maung
*Assistant Examiner* — Jose Torres
(74) *Attorney, Agent, or Firm* — Lucas & Mercanti, LLP

(57) ABSTRACT

A dynamic analysis system includes a diagnostic console which calculates at least one index value representing variation in a target portion of a human body from at least one dynamic image acquired by performing radiographic imaging to a subject containing the target portion, and evaluates flexibility of the target portion based on the calculated index value.

19 Claims, 9 Drawing Sheets

(56) References Cited

U.S. PATENT DOCUMENTS

| | | | |
|---|---|---|---|
| 2011/0019886 A1* | 1/2011 | Mizuno | G06T 7/0014 |
| | | | 382/128 |
| 2011/0237938 A1* | 9/2011 | Mizuno | G06T 7/0012 |
| | | | 600/425 |
| 2011/0243403 A1* | 10/2011 | Mizuno | G06T 7/0012 |
| | | | 382/128 |
| 2012/0130238 A1* | 5/2012 | Muraoka | A61B 6/4233 |
| | | | 600/436 |
| 2013/0156267 A1* | 6/2013 | Muraoka | A61B 6/5217 |
| | | | 382/103 |
| 2015/0042677 A1* | 2/2015 | Shimamura | A61B 6/4233 |
| | | | 345/632 |
| 2015/0245776 A1* | 9/2015 | Hirohata | A61B 6/032 |
| | | | 600/504 |
| 2016/0163062 A1* | 6/2016 | Garber | A61B 5/0536 |
| | | | 382/131 |

FOREIGN PATENT DOCUMENTS

| | | |
|---|---|---|
| JP | 2009-207518 A | 9/2009 |
| JP | 4404291 B2 | 11/2009 |
| JP | 5093727 B2 | 9/2012 |
| JP | 2013-504394 A | 2/2013 |
| WO | 2012/026145 A1 | 3/2012 |
| WO | 2015/023495 A1 | 2/2015 |

OTHER PUBLICATIONS

JPO, Office Action issued in the corresponding Japanese Patent Application No. 2016-063125, dated Jan. 14, 2020, with English translation.

* cited by examiner

DYNAMIC ANALYSIS SYSTEM

CROSS-REFERENCE TO RELATED APPLICATIONS

This application is based upon and claims the benefit of priority from the prior Japanese Patent Application No. 2016-063125 filed on Mar. 28, 2016, the entire contents of which are incorporated herein by reference.

BACKGROUND OF THE INVENTION

Field of the Invention

The present invention relates to a dynamic analysis system.

Description of Related Art

Traditional acquisition of static radiographic (X-ray) images has used a film/screen or photostimulable phosphor plate to assist medical diagnosis. Recent studies have focused on acquiring a dynamic image of a portion to be inspected (hereinafter referred to as "target portion") using a semiconductor image sensor (e.g., a flat panel detector (FPD)) and applying the image to medical diagnosis. This technique is based on the quick responsibility of the semiconductor image sensor in reading and deleting image data. In detail, the technique involves continuous emission of pulsed radiation from a radiation source in accordance with the timings of reading and deletion of the semiconductor image sensor, and acquisition of multiple images per second to capture dynamic states of the target portion. The series of acquired images are sequentially displayed to allow a doctor to observe a series of movements of the target portion.

In inspection of lungs, detection of a portion having a defective function (ventilatory or blood flow function) has high importance. Unfortunately, doctors cannot readily find a portion having a defective function based on visual observation of a dynamic image. In particular, the individual variations in respiratory movements of lungs and heartbeats make it harder to visually recognize a portion having a defective ventilatory or blood flow function.

To solve this problem, some systems analyze dynamic images acquired by dynamic imaging and generate diagnosis-assisting information to be provided to doctors for early diagnosis.

For example, PTL 1 (Japanese Patent No. 4404291) discloses a system that generates differential images between frames of a dynamic image during respiration. The system then determines a differential pixel having the maximum absolute value in each group of corresponding pixels of the differential images between frames, and generates a maximum-value image consisting of these differential pixels. The system displays the generated image superimposed on an image in a predetermined respiratory phase.

PTL 2 (Japanese Patent No. 5093727) discloses a system that calculates pixel values within a predetermined range in each of the frame images constituting an X-ray dynamic image, and generates blood-flow information indicating a temporal variation in the pixel values varying in response to heartbeats. The system also detects a boundary portion between a lung field region and a heart in each frame image, and calculates the movement of the boundary portion as the movement of a core wall.

Measurement of lung compliance is considered effective to diagnose respiratory problems. The lung compliance is an index indicating the flexibility of a lung. A lung having high lung compliance readily expands. This lung has low elastic recoil and causes excess expansion, and thus precludes rapid expiration. In other words, this lung does not readily contract. The lung having high lung compliance may have problems, such as pulmonary emphysema, COPD, and a pulmonary cystic disease. In contrast, a lung having low lung compliance is inflexible and cannot sufficiently expand regardless of movement of inspiratory muscles. In other words, this lung does not readily expand, and readily contracts. The lung having low lung compliance may have problems, such as a restrictive lung disease, interstitial pneumonia, pulmonary fibrosis, and pulmonary edema.

The lung compliance is measured by inserting a tube through the nose to the esophagus and detecting the pressure in the esophagus. Unfortunately, this method places a large burden on a test subject, requires large tasks, and cannot provide any stable value, and thus is not practically applied. Another problem of the method is that it cannot provide local lung compliances, despite differences in lung compliance from place to place in a diseased lung.

Measurement of the flexibility (hardness) of pulmonary vessels is considered effective to diagnose arteriosclerosis and pulmonary hypertension. The hardness of blood vessels is generally measured. For example, four sphygmomanometers are mounted on the right and left arms and ankles to contemporarily measure blood pressures. In diagnosis of arteriosclerosis, the vascular diameter in the neck is determined by echography.

Unfortunately, these methods for measuring the hardness of blood vessels cannot be applied to the evaluation of the flexibility of pulmonary vessels.

The system disclosed in PTL 1 or 2 analyzes a dynamic image to calculate information effective in inspection of the ventilatory and blood flow functions of a lung, but cannot determine the flexibility of a lung field or pulmonary vessels.

SUMMARY OF THE INVENTION

An object of the present invention is to enable evaluating flexibility of a target portion based on a dynamic image.

To achieve the above object, a dynamic analysis system in which one aspect of the present invention is reflected includes: a diagnostic console which calculates at least one index value representing variation in a target portion of a human body from at least one dynamic image acquired by performing radiographic imaging to a subject containing the target portion, and evaluates flexibility of the target portion based on the calculated index value.

BRIEF DESCRIPTION OF THE DRAWINGS

The present invention will become more fully understood from the detailed description given hereinbelow and the appended drawings, and thus are not intended as a definition of the limits of the present invention, and wherein.

PREFERRED EMBODIMENT OF THE PRESENT INVENTION

Embodiments of the invention will now be described in detail with reference to the accompanying drawings. The illustrated examples should not be construed to limit the present invention.

[Configuration of Dynamic Analysis System 100]

The configuration will now be described.

Figure 1:
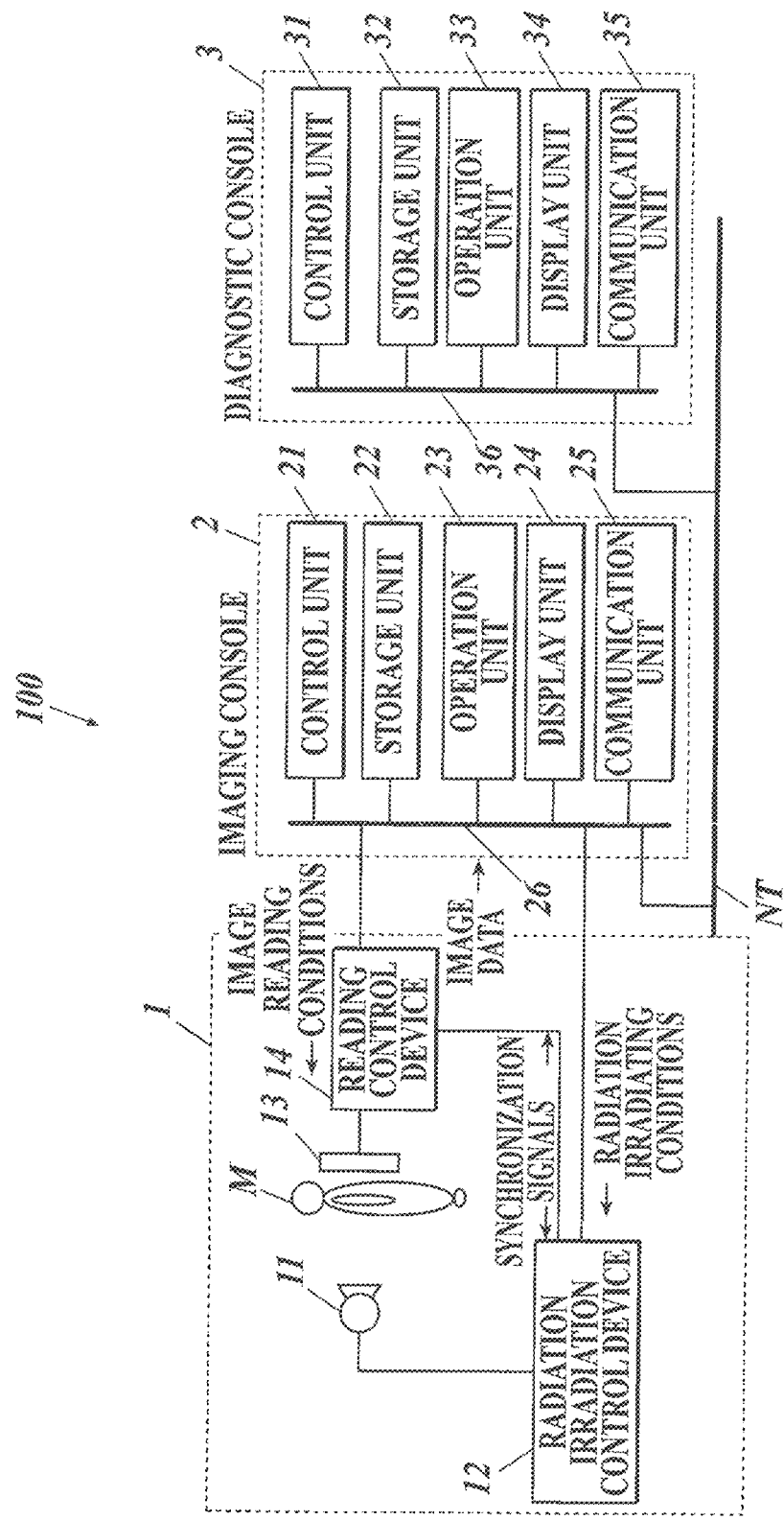
FIG. 1 illustrates an entire configuration of a dynamic analysis system according to an embodiment of the present invention.

FIG. 1 illustrates the entire configuration of the dynamic analysis system 100 according to an embodiment of the present invention.

With reference to FIG. 1, the dynamic analysis system 100 includes an imaging apparatus 1, an imaging console 2, and a diagnostic console 3. The imaging apparatus 1 is connected to the imaging console 2 with communication cables, whereas the imaging console 2 is connected to the diagnostic console 3 via a communication network NT, such as a local area network (LAN). The components of the dynamic analysis system 100 are compatible with the standard of digital image and communications in medicine (DICOM), and communicate with each other according to the DICOM standard.

[Configuration of Imaging Apparatus 1]

The imaging apparatus 1 is an imaging member which captures periodically (cyclically) dynamic states, such as deformation (expansion and contraction) of a lung during respiration and heartbeats, by dynamic imaging. The dynamic imaging indicates acquisition of multiple images that represent the dynamic states by repeated irradiation (pulse irradiation) of a subject with pulsed radiation (e.g., X-rays) in a predetermined time interval or continuous (uninterrupted) irradiation at a low dose rate. A series of images acquired by the dynamic imaging is called a dynamic image. The images constituting the dynamic image are called frame images. The following description of embodiments focuses on the dynamic imaging by pulse radiation.

A radiation source 11 is disposed at a position opposing to a radiation detector 13 with a subject M therebetween. The radiation source 11 irradiates the subject M with radiation (X-rays) under the control of a radiation irradiation control device 12.

The radiation irradiation control device 12 is connected to the imaging console 2, and controls the radiation source 11 to perform radiographic imaging under the radiation irradiating conditions input from the imaging console 2. Examples of the radiation irradiating conditions input from the imaging console 2 include pulse rate, pulse width, pulse interval, the number of frames acquired in a single imaging process, X-ray tube current value, X-ray tube voltage value, and the type of an added filter. The pulse rate indicates the number of irradiation times with radiation per second and accords with the frame rate (described below). The pulse width indicates the period of a single radiating irradiation. The pulse interval indicates the time from the start of a radiating irradiation to the start of the subsequent radiating irradiation and accords with the frame interval (described below).

The radiation detector 13 is composed of a semiconductor image sensor, such as an FPD. The FPD has, for example, a glass substrate and multiple detecting elements (pixels) disposed in a matrix at predetermined positions on the substrate. The detecting elements detect radiation, depending on their intensities, emitted from the radiation source 11 and passing through at least the subject M, and accumulate electrical signals converted from the detected radiation therein. Each pixel is equipped with a switching part including a thin film transistor (TFT), for example. The FPD may be of an indirect conversion type that converts X-rays into light with a scintillator and then the light into electrical signals with a photoelectric converter and a direct conversion type that directly converts X-rays into electrical signals.

The radiation detector 13 is disposed at a position opposing to the radiation source 11 with the subject M therebetween.

A reading control device 14 is connected to the imaging console 2. The reading control device 14 controls the switching parts of the pixels of the radiation detector 13 on the basis of the image reading conditions input from the imaging console 2 to switch reading of the electrical signals accumulated in the pixels so as to sequentially read the electrical signals accumulated in the radiation detector 13. The image data is thus obtained. This image data corresponds to frame images. The reading control device 14 then outputs the acquired frame images to the imaging console 2. Examples of the image reading conditions include frame rate, frame interval, pixel size, and image size (matrix size). The frame rate indicates the number of frame images acquired per second and accords with the pulse rate. The frame interval indicates the time from the start of acquisition of a frame image to the start of acquisition of the subsequent frame image and accords with the pulse interval.

The radiation irradiation control device 12 and the reading control device 14 are connected to each other, and synchronize the radiation irradiating operation with the image reading operation through transmission of synchronization signals therebetween.

[Configuration of Imaging Console 2]

The imaging console 2 outputs the radiation irradiating conditions and/or image reading conditions to the imaging apparatus 1 to control radiographic imaging and reading operations of radiographic images by the imaging apparatus 1. The imaging console 2 displays the dynamic image acquired by the imaging apparatus 1 to allow an operator (e.g., a radiologist) to check positioning and determine the image to be appropriate for medical diagnosis.

With reference to FIG. 1, the imaging console 2 includes a control unit 21, a storage unit 22, an operation unit 23, a display unit 24, and a communication unit 25, which are connected to each other with buses 26.

The control unit 21 includes a central processing unit (CPU) and a random access memory (RAM). In response to manipulation to the operation unit 23, the CPU of the control unit 21 reads a system program and various processing programs from the storage unit 22, loads the programs in the RAM, and executes various processes, such as an imaging control process (described below), under the instructions of the loaded programs. The control unit 21 thereby comprehensively controls the operations of the individual units of the imaging console 2 and the radiation irradiating and reading operations of the imaging apparatus 1.

The storage unit 22 includes a nonvolatile semiconductor memory or a hard disk. The storage unit 22 stores various programs to be executed in the control unit 21, parameters required for process execution under the instructions of the programs, and/or results of the processes. For example, the storage unit 22 stores a program for execution of the imaging control process illustrated in FIG. 2. The storage unit 22 also stores the radiation irradiating conditions and the image reading conditions in association with portions to be imaged. The programs are stored in the form of computer-readable program codes, and the control unit 21 sequentially executes operations under the instructions corresponding to the program codes.

The operation unit 23 includes a keyboard having cursor keys, numeric keys, and various functional keys; and a pointing device (e.g., a mouse). The operation unit 23 receives instruction signals input by manipulation to the keyboard or mouse and outputs the signals to the control unit 21. The operation unit 23 may also include a touch panel on the screen of the display unit 24. In this case, the operation unit 23 receives instruction signals input through the touch panel and outputs the signals to the control unit 21.

The display unit 24 includes a monitor, such as a liquid crystal display (LCD) or a cathode ray tube (CRT) display. The display unit 24 displays instructions input through the operation unit 23 and data, for example, under the instructions corresponding to display signals input from the control unit 21.

The communication unit 25 includes a LAN adapter, a modem, or a terminal adapter (TA). The communication unit 25 controls data communication between the individual devices/apparatuses connected to the communication network NT.

[Configuration of Diagnostic Console 3]

The diagnostic console 3 receives a dynamic image from the imaging console 2 and displays the received dynamic image and the analytical results on the dynamic image to assist diagnosis by a doctor.

With reference to FIG. 1, the diagnostic console 3 includes a control unit 31, a storage unit 32, an operation unit 33, a display unit 34, and a communication unit 35, which are connected to each other with buses 36.

The control unit 31 includes a CPU and a RAM. In response to manipulation to the operation unit 33, the CPU of the control unit 31 reads a system program and various processing programs from the storage unit 32, loads the programs in the RAM, and executes various processes, such as an image analyzing process (described below), under the instructions of the loaded programs. The control unit 31 thereby comprehensively controls the operations of the individual units of the diagnostic console 3.

The storage unit 32 includes a nonvolatile semiconductor memory or a hard disk. The storage unit 32 stores various programs (e.g., a program for execution of the image analyzing process by the control unit 31), parameters required for process execution under the instructions of the programs, and/or results of the processes. These programs are stored in the form of computer-readable program codes, and the control unit 31 sequentially executes operations under the instructions corresponding to the program codes.

The storage unit 32 also stores a reference value of an index value representing variation in a lung field, the variation corresponding to at least one of physical characteristics (e.g., height, weight, age, sex, respiratory strategy, volume and area of the lung field, and respiratory rate), such that the reference value is associated with the at least one of physical characteristics. The storage unit 32 also stores a reference value of an index value representing variation in each pulmonary vessel, the variation corresponding to at least one of physical characteristics (e.g., age, sex, volume and area of the heart, and heart rate), such that the reference value is associated with the at least one of physical characteristics.

The operation unit 33 includes a keyboard having cursor keys, numeric keys, and various functional keys; and a pointing device (e.g., a mouse). The operation unit 33 receives instruction signals input by manipulation to the keyboard or mouse and outputs the signals to the control unit 31. The operation unit 33 may also include a touch panel on the screen of the display unit 34. In this case, the operation unit 33 receives instruction signals input through the touch panel and outputs the signals to the control unit 31.

The display unit 34 includes a monitor, such as an LCD or a CRT display. The display unit 34 performs various displays under the instructions corresponding to display signals input from the control unit 31.

The communication unit 35 includes a LAN adapter, a modem, or a TA. The communication unit 35 controls data communication between the individual devices/apparatuses connected to the communication network NT.

[Operation of Dynamic Analysis System 100]

The operation of the dynamic analysis system 100 will now be explained.

(Operation of Imaging Apparatus 1 and Imaging Console 2)

The imaging operation of the imaging apparatus 1 and the imaging console 2 will now be explained.

Figure 2:
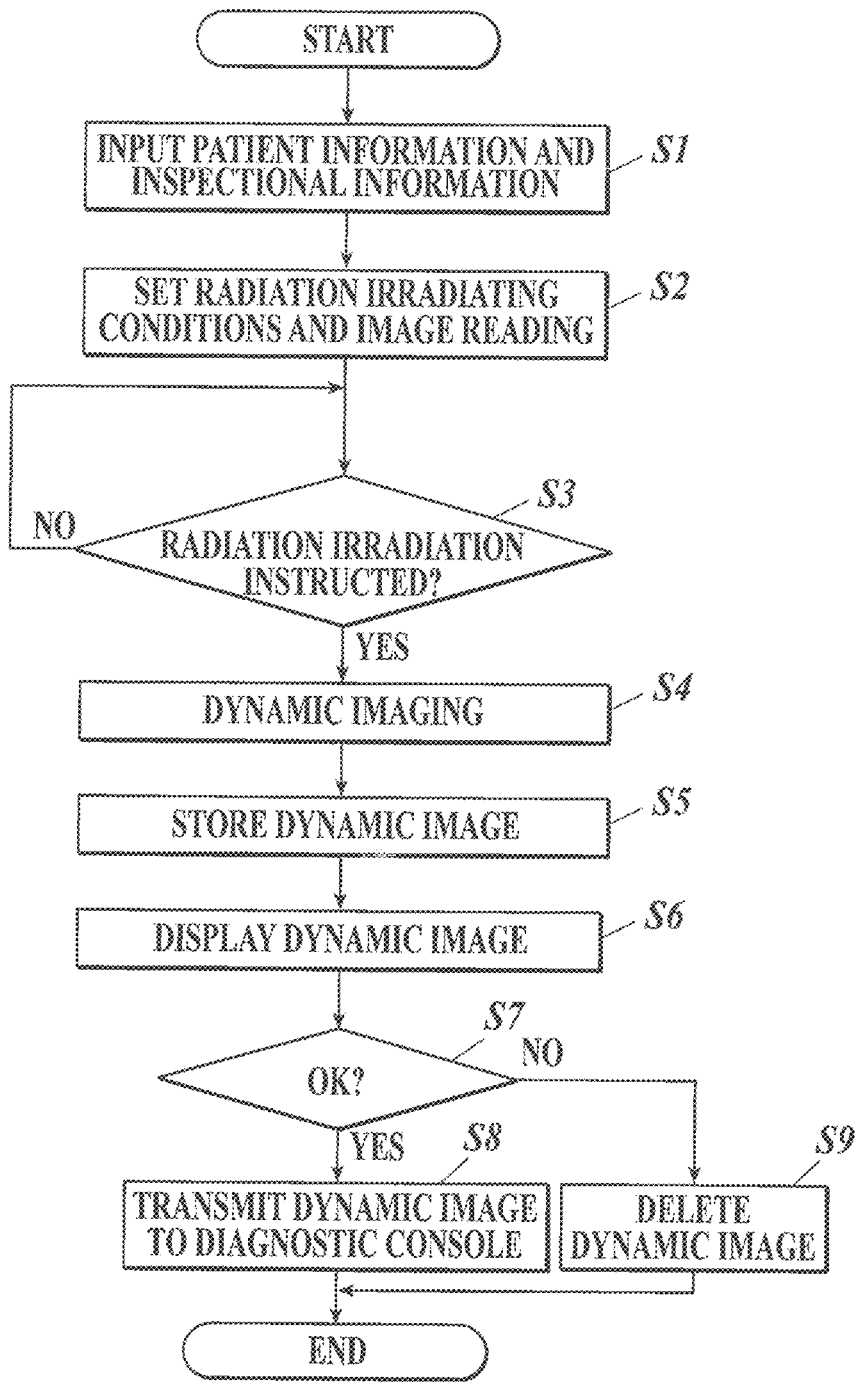
FIG. 2 is a flowchart illustrating an imaging control process executed by a control unit of an imaging console in FIG. 1.

FIG. 2 illustrates an imaging control process executed by the control unit 21 of the imaging console 2. The control unit 21 executes the imaging control process in cooperation with the program stored in the storage unit 22.

An operator manipulates the operation unit 23 of the imaging console 2 to input patient information (e.g., name, height, weight, age, and sex of a patient) on a test subject (subject M) and inspectional information (e.g., portion to be imaged (breast in this embodiment) and respiratory strategy (deep breathing or quiet breathing)) (Step S1).

The radiation irradiating conditions are then read from the storage unit 22 and set in the radiation irradiation control device 12, whereas the image reading conditions are read from the storage unit 22 and set in the reading control device 14 (Step S2).

The control unit 21 waits for a radiation irradiation instruction to be input by manipulation to the operation unit 23 (Step S3). The operator then places the subject M at a position between the radiation source 11 and the radiation detector 13 and performs positioning. The operator instructs the test subject (subject M) to relax and take quiet breathing, so as to take a dynamic image during respiration in the embodiment. Alternatively, the operator may guide the subject M to take deep breathing by words "Inhale, then exhale," for example. After completion of preparation for imaging, the operator manipulates the operation unit 23 to input a radiation irradiation instruction.

In response to input of the radiation irradiation instruction through the operation unit 23 (Step S3; YES), the control unit 21 outputs an initiation instruction to the radiation irradiation control device 12 and the reading control device 14 to initiate the imaging operation (Step S4). Concretely, the radiation source 11 emits radiation in the pulse interval set in the radiation irradiation control device 12, and the radiation detector 13 acquires frame images.

After a predetermined number of frame-image acquisitions, the control unit 21 outputs a termination instruction to the radiation irradiation control device 12 and the reading control device 14 to terminate the imaging operation. The number of acquired frame images is equal to or larger than the number of frame images for a single respiratory cycle.

The frame images acquired by imaging are sequentially input to the imaging console 2 and stored in the storage unit 22 in association with the frame number indicating the imaging order (Step S5), and are displayed on the display unit 24 (Step S6). The operator checks the positioning and the like based on the displayed dynamic image, and then determines the acquired image to be appropriate for medical diagnosis (in the case of successful imaging operation) or to need reacquisition (in the case of unsuccessful imaging operation). The operator manipulates the operation unit 23 to input the result of the determination.

In response to input of the determination result indicating successful imaging operation through predetermined manipulation to the operation unit 23 (Step S7; YES), information (e.g., information for identifying the dynamic image (identification ID), patient information, inspectional information, radiation irradiating conditions, image reading conditions, and the frame number indicating the imaging order) is added to each of the series of frame images acquired in the dynamic imaging operation (e.g., written in the header of data on the image in the DICOM format). The frame images are then transmitted to the diagnostic console 3 via the communication unit 25 (Step S8). The imaging control process is then terminated. In response to input of the determination result indicating unsuccessful imaging operation through predetermined manipulation to the operation unit 23 (Step S7; NO), the series of frame images are deleted from the storage unit 22 (Step S9). The imaging control process is then terminated. In this case, the imaging operation must be performed again.

(Operation of Diagnostic Console 3)

The operation in the diagnostic console 3 will now be explained.

Figure 3:
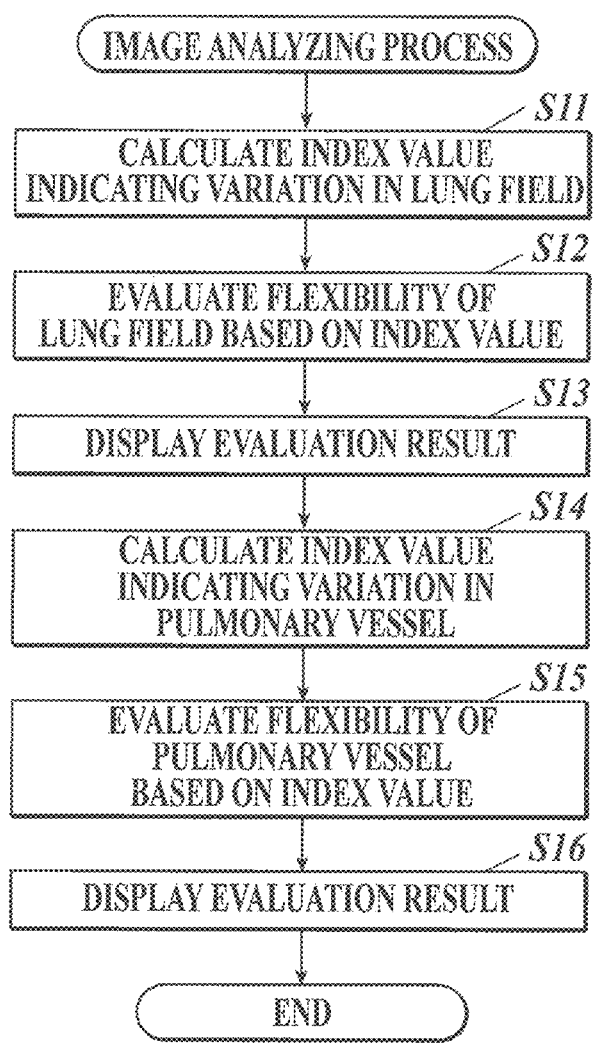
FIG. 3 is a flowchart illustrating an image analyzing process executed by a control unit of a diagnostic console in FIG. 1.

If the diagnostic console 3 receives the series of frame images of the dynamic image from the imaging console 2 via the communication unit 35, the control unit 31 executes an image analyzing process illustrated in FIG. 3 in cooperation with the program stored in the storage unit 32.

The flow of the image analyzing process will now be explained with reference to FIG. 3.

The control unit 31 calculates the index value representing variation in the lung field based on the dynamic image (Step S11).

Figure 4:
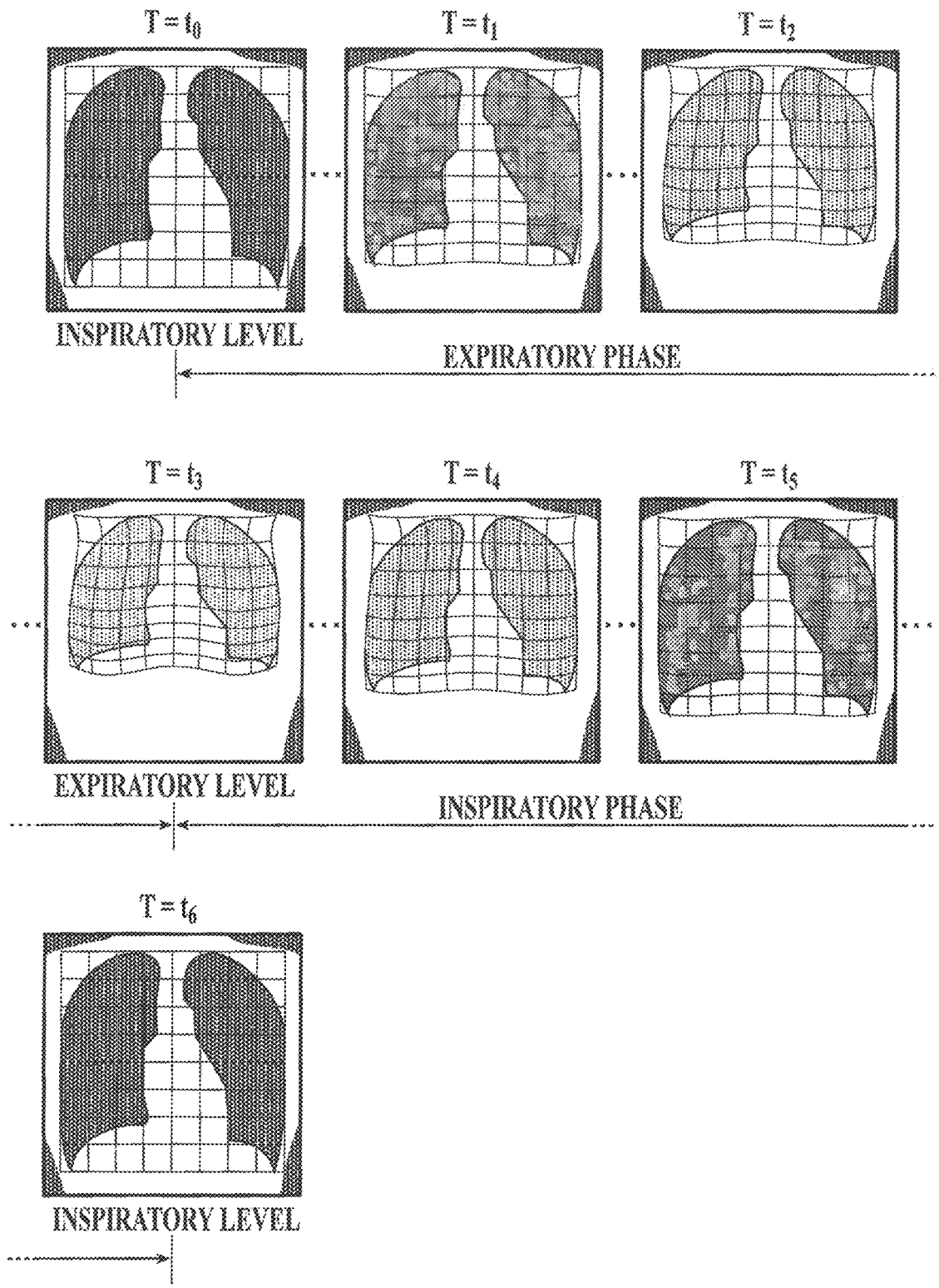
FIG. 4 illustrates variation in a lung field during a respiratory movement.

FIG. 4 illustrates the frame images in plural time phases T (T=$t_0$ to $t_6$) captured during respiration. With reference to FIG. 4, a respiratory cycle consists of an expiratory phase and an inspiratory phase. In the expiratory phase, the diaphragm ascends to exhaust air from the lung, thereby decreasing a lung field region as illustrated in FIG. 4. This increases density of the lung field, and the lung field is thus rendered with a low signal value (density value) in the dynamic image. In addition, the periphery of the thorax shifts inward. The diaphragm resides at the highest position at the expiratory level (i.e., resting expiratory level or maximum expiratory level). In the inspiratory phase, the diaphragm descends to introduce air into the lung, thereby increasing the lung field region in the thorax as illustrated in FIG. 4. This decreases the density of the lung field, and the lung field is thus rendered with a high signal value in the dynamic image. In addition, the periphery of the thorax shifts outward. The diaphragm resides at the lowest position at the inspiratory level (i.e., resting inspiratory level or maximum inspiratory level). In other words, the movement of the lung field is in connection with the movements of the diaphragm and the periphery of the thorax.

As the index value representing variation in the lung field, for example, at least one of the following values (1) to (8) is calculated:

(1) a variation in density of the lung field
(2) a variation in area of the lung field (a moving amount of the contour of the lung field)
(3) a movement of the diaphragm (a moving amount of the diaphragm)
(4) a movement of the periphery of the thorax (a moving amount of the periphery of the thorax)
(5) a rate of variation in density of the lung field
(6) a rate of variation in area of the lung field
(7) a rate of movement of the diaphragm
(8) a rate of movement of the periphery of the thorax Procedures of calculating the index values (1) to (8) will now be explained.

(1) Variation in Density of the Lung Field

Figure 5:
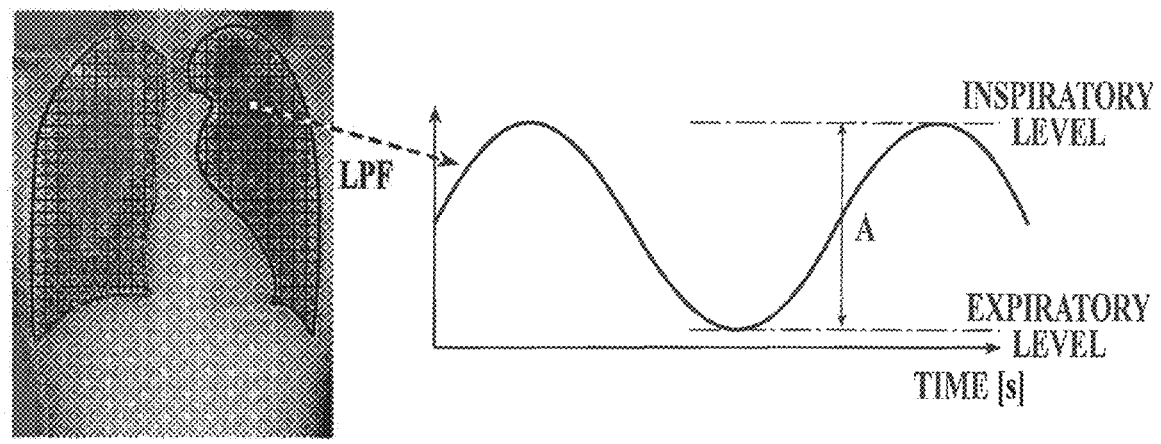
FIG. 5 is a schematic diagram illustrating a procedure of calculating a variation in density of the lung field.

FIG. 5 is a schematic diagram illustrating a procedure of calculating the variation in density of the lung field.

With reference to FIG. 5, the lung field region in each frame image is divided into subregions (e.g., three rectangular regions (upper, middle, and lower lung fields) each having a predetermined size). These subregions are then correlated with the respective subregions of the other frame images. For each subregion, a representative value (e.g., an average or median value) of signal values (density values) of the pixels in the subregion is calculated. The calculated representative value is substituted for the signal values of the pixels in the subregion. The temporal variation in the substituted representative value is then subject to a low-pass filtering (LPF) process in the time domain. In a single respiratory cycle of the wave graph representing the temporal variation in signal value after the low-pass filtering process, the difference (A in FIG. 5) or the ratio between the maximum value (at the inspiratory level) and the minimum value (at the expiratory level) is calculated as the variation in density of the lung field.

The lung field region may be extracted by any technique. An example technique for extracting the lung field region involves: acquisition of the threshold value based on the histogram of the signal values of the pixels by discriminant analysis; primary extraction of a region having signal values higher than the threshold value as a candidate of the lung field region; edge detection around the boundary (contour) of the candidate lung field region; and extraction of edge points having the maximum signal differences along the boundary from subregions around the boundary.

An example technique of dividing each frame image into subregions and correlating the subregions between the frame images involves: selecting the frame image (at the expiratory level) having the smallest lung field region from the frame images of the dynamic image as the reference image; dividing the lung field region in the reference image into multiple subregions; dividing the other frame images into subregions such that each subregion has identical pixel positions to those of the corresponding subregion in the reference image; and correlating the subregions having the same pixel positions with each other between the frame images.

The low-pass filtering process in the time domain removes high-frequency variations in signal value caused by the blood flow from the dynamic image, to extract the temporal variation in signal value (temporal frequency components at low frequency) caused by the ventilation. For example, the temporal variation in signal value in each subregion is extracted with a filter having a cutoff frequency of 0.85 Hz.

(2) Variation in Area of the Lung Field

The variation in area of the lung field is calculated as the movement of the contour of the lung field. First, the lung field region is extracted from each frame image of the dynamic image. Second, the area of the lung field region in each frame image is calculated by multiplying the pixel size by the number of pixels in the lung field region. The variation in area of the lung field is determined by calculating the difference or ratio between the maximum lung-field area (at the inspiratory level) and the minimum lung-field area (at the expiratory level) in a single respiratory cycle.

(3) Movement of the Diaphragm

Figure 6:
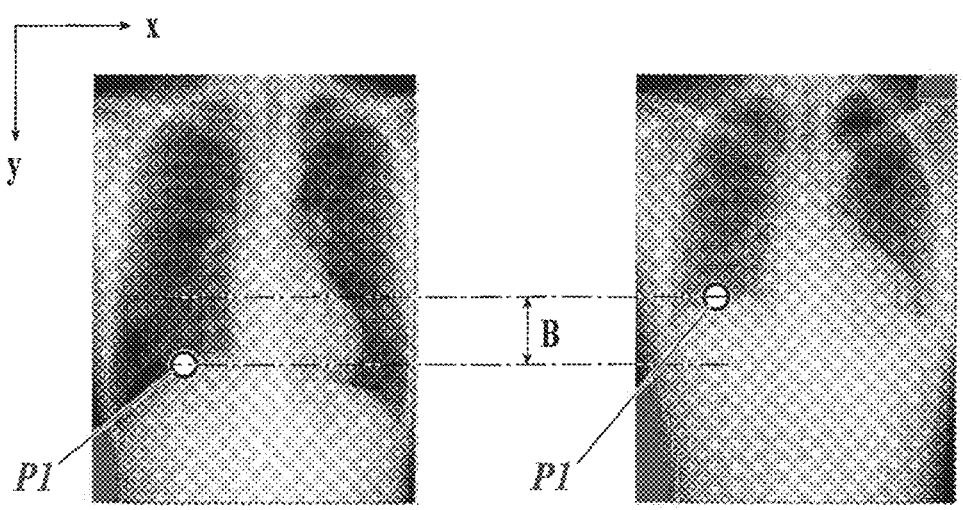
FIG. 6 is a schematic diagram illustrating a procedure of calculating a movement of a diaphragm.

FIG. 6 is a schematic diagram illustrating a procedure of calculating the movement of the diaphragm.

The reference position P1 of the diaphragm is determined in each frame image of the dynamic image. An example technique involves: extraction of a bottom edge region of the lung field region, as a diaphragm border region, from each frame image; and determination of the reference position P1 at a certain x-coordinate in the diaphragm border region. The movement of the diaphragm is determined by calculating the difference (B in FIG. 6) or ratio between the maximum and minimum values of y-coordinates of the reference position P1 in the frame images in a single respiratory cycle.

(4) Movement of the Periphery of the Thorax

Figure 7A:
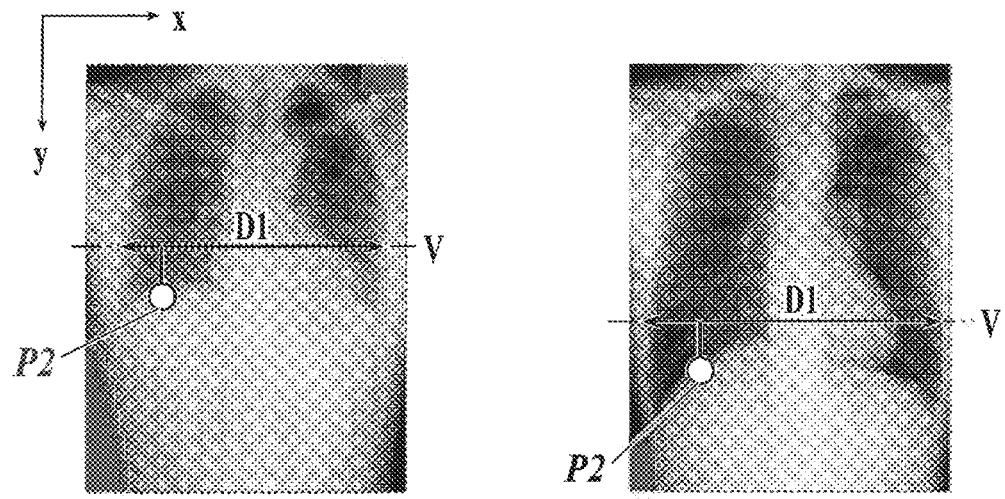
FIG. 7A is a schematic diagram illustrating a procedure of calculating a movement of a periphery of a thorax.
Figure 7B:
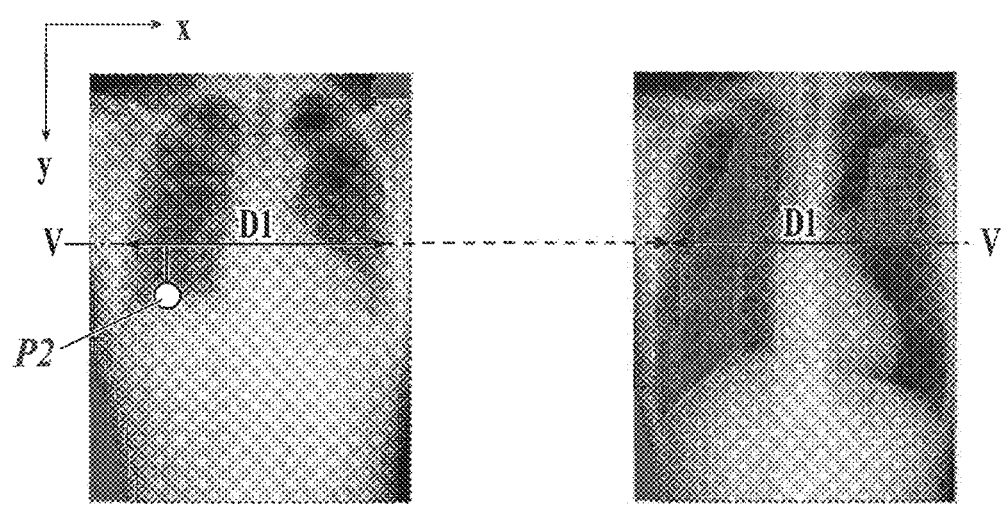
FIG. 7B is a schematic diagram illustrating a procedure of calculating the movement of the periphery of the thorax.

In the first step of calculating the movement of the periphery of the thorax, a reference y-coordinate V (reference position in a vertical direction) of the periphery of the thorax is determined in each frame image of the dynamic image. The reference y-coordinates V can be determined by either of the two techniques: (i) determination of the reference y-coordinates V having the clinically identical positions; and (ii) determination of the reference y-coordinates V having the identical pixel positions. The technique (i) (refer to FIG. 7A) involves determination of the point P2 at a certain x-coordinate along the diaphragm border in each frame image, and determination of the reference y-coordinate V distant from the y-coordinate of the point P2 by a predetermined height in a vertical direction in each frame image. The technique (ii) (refer to FIG. 7B) involves selection of the reference image including the diaphragm at the highest position, determination of the point P2 at a certain x-coordinate along the diaphragm border in the reference image, determination of the reference y-coordinate V distant from the y-coordinate of the point P2 by a predetermined height in a vertical direction in the reference image, and setting of the reference y-coordinate V of each of the other frame images at the same position as the reference y-coordinate V in the reference image. The technique (i) can more accurately reflect the respiratory states, whereas the technique (ii) is simpler because it does not require determination of the reference y-coordinates V in the individual frame images.

The distance between the opposite peripheries of the thorax, namely, the distance D1 between the right and left edges of the lung field region at the reference y-coordinate V is then calculated in each frame image of the dynamic image in a single respiratory cycle. The movement of the periphery of the thorax is determined by calculating the difference or ratio between the maximum and minimum values of the calculated distance D1.

(5) Rate of Variation in Density of the Lung Field

The rate of variation in density of the lung field can be calculated by dividing the variation in density of the lung field by the inspiratory time. The inspiratory time indicates the time from the minimum to maximum signal values in a single respiratory cycle of the wave graph representing the temporal variation in density after the low-pass filtering process. The inspiratory time may be replaced with the expiratory time (the time from the maximum to minimum signal values in the above wave graph).

(6) Rate of Variation in Area of the Lung Field

The rate of variation in area of the lung field can be calculated by dividing the variation in area of the lung field by the inspiratory time. The inspiratory time indicates the time from the minimum to maximum areas. The inspiratory time may be replaced with the expiratory time (the time from the maximum to minimum areas).

(7) Rate of Movement of the Diaphragm

The rate of movement of the diaphragm can be calculated by dividing the movement of the diaphragm by the inspiratory time. The inspiratory time indicates the time from the minimum to maximum y-coordinates of the reference position P1. The inspiratory time may be replaced with the expiratory time.

(8) Rate of Movement of the Periphery of the Thorax

The rate of movement of the periphery of the thorax can be calculated by dividing the movement of the periphery of the thorax by the inspiratory time. The inspiratory time indicates the time of the minimum to maximum distance D1 between the opposite peripheries of the thorax at the reference y-coordinate V.

On the basis of the calculated index values representing variations in the lung, the flexibility of the lung field is evaluated (Step S12).

For example, in the case of any one of the index values (1) to (4) calculated in Step S11, the control unit 31 acquires the range (reference range) of the reference value of the index value, which corresponds to the test subject's physical characteristics (e.g., height, weight, age, sex, respiratory strategy, and volume of the lung field) added to the dynamic image and/or corresponds to the area of the lung field calculated from the dynamic image, from the storage unit 32. Then the flexibility of the lung field is evaluated based on comparison of the index value calculated in Step S11 with the acquired reference range.

In the case of any one of the index values (5) to (8) calculated in Step S11, the control unit 31 acquires the reference range of index value, which corresponds to the subject's physical characteristics (e.g., respiratory strategy and volume of the lung field) added to the dynamic image and/or corresponds to the area of the lung field and/or the respiratory rate calculated from the dynamic image, from the storage unit 32. Then the flexibility of the lung field is evaluated based on comparison of the index value calculated in Step S11 with the acquired reference range. The respiratory rate (e.g., the respiratory rate per minute) can be calculated based on the respiratory cycle acquired from the wave graph representing the variation in density of the lung field, for example.

For a larger index value calculated in Step S11, the lung field is evaluated more flexible. For example, the lung field is evaluated more flexible than normal for the index value calculated in Step S11 that exceeds the reference range. The lung field is evaluated normal for the index value calculated in Step S11 that is within the reference range. The lung field is evaluated less flexible than normal for the index value calculated in Step S11 that falls below the reference range. The deviation of the index value calculated in Step S11 from the reference range is calculated as an evaluated value indicating the flexibility of the lung field.

The display unit 34 then displays an evaluation result screen indicating the results of evaluation (Step S13).

Figure 8:
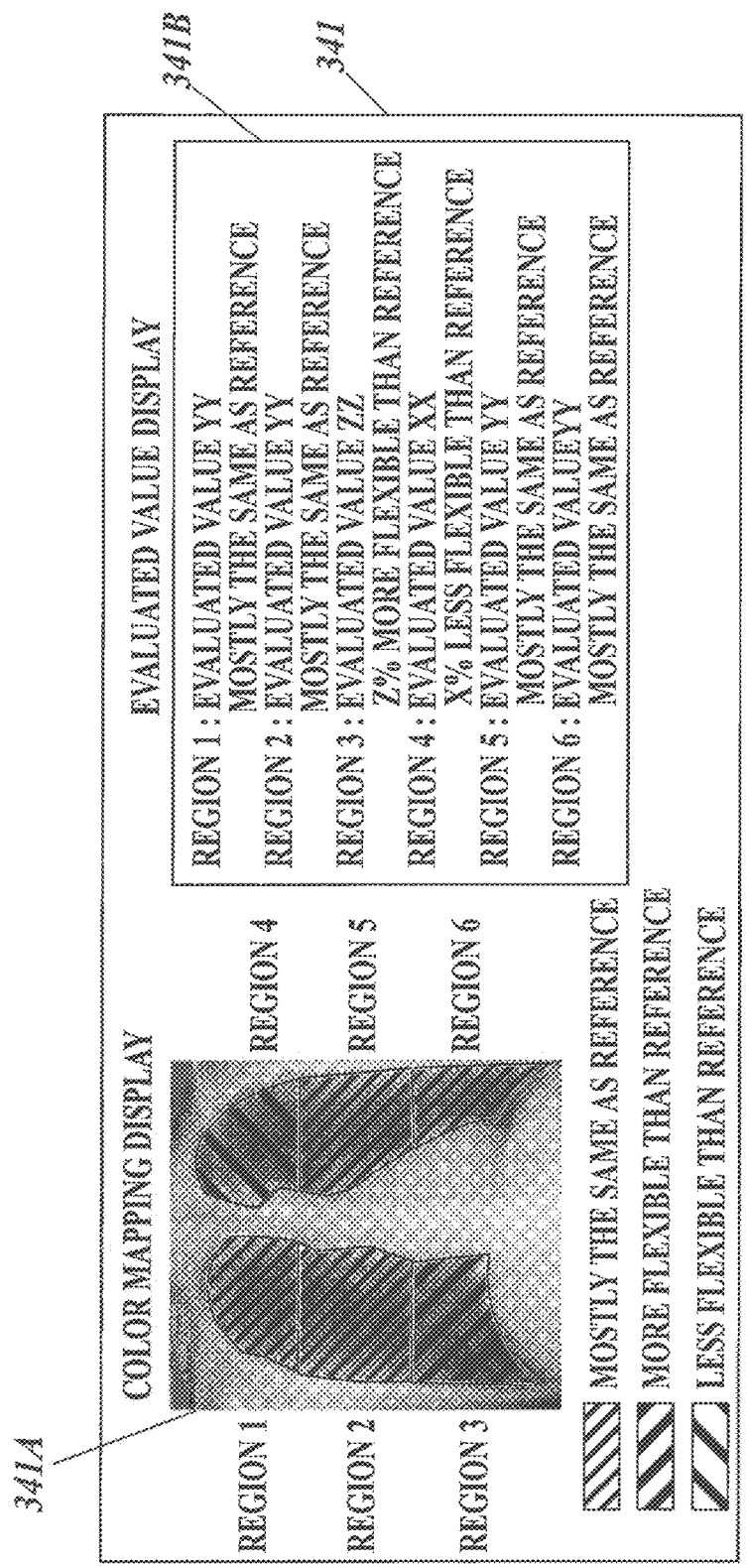
FIG. 8 illustrates an example evaluation result screen.

FIG. 8 illustrates an example of the evaluation result screen 341 displayed in Step S13. With reference to FIG. 8, the evaluation result screen 341 includes a color mapping display 341A where subregions have different colors corresponding to the evaluation results (more flexible than normal, normal, and less flexible than normal) on the reference image, and an evaluated value display 341B where the evaluated values of the respective subregions are displayed with numeric values. The evaluated value display 341B may always display the evaluated values of all the subregions as illustrated in FIG. 8, or may display only the evaluated value of the subregion designated on the image in the color mapping display 341A by the operation unit 33 (clicked or pointed with the cursor). The display of the values of all the subregions can facilitate comprehensive observation. The display of the value of the designated subregion alone allows the operator to focus on the value of the subregion of interest without being distracted by unnecessary information, regardless of an increase in the number of subregions.

The index value representing variation in the pulmonary vessel is then calculated from the dynamic image (Step S14).

As the index value representing variation in the pulmonary vessel, at least one of the following values (9) to (14) is calculated:

(9) a deformation of a pulmonary vessel

(10) a variation in diameter of a pulmonary vessel (hereinafter referred to as "variation in vascular diameter")

(11) a rate of variation in density of the pulmonary vessels

(12) a rate of variation in diameter of a pulmonary vessel (hereinafter referred to as "rate of variation in vascular diameter")

(13) a rate of variation in density of a pulmonary vessel between two sites

(14) a rate of variation in vascular diameter between two sites

Procedures of calculating the index values (9) to (14) will now be explained.

(9) Deformation of a Pulmonary Vessel

A pulmonary vessel contracts and curves during no blood flow, and expands and unbends in response to blood flow. The variation in curvature of a pulmonary vessel is thus defined as the deformation of the pulmonary vessel.

First, the pulmonary vessels are extracted from the lung field regions in respective frame images and then labeled. Second, the curvatures of the extracted pulmonary vessels (provided with the identical labels, which are described below) are calculated in the respective frame images. Third, based on these vessels, the deformation of the pulmonary vessel is determined by calculating the ratio (a/b) or difference (a−b) between the curvatures a and b, where a indicates the highest curvature of the pulmonary vessel in a contracted and steeply curved mode, and b indicates the lowest curvature of the pulmonary vessel in an expanded and gently curved mode.

The vessel region can be extracted from the lung field region by, for example, a template matching process with a prepared vessel template image. The vessel template image is an image representing the general network of pulmonary vessels in the lung field region, where the individual pulmonary vessels are provided with the unique labels (label names). For example, the template matching process involves searching for a pulmonary vessel in each frame image that has a corresponding shape to that of a uniquely-labeled vessel in the vessel template image, and providing the region including this pulmonary vessel with the same label as the vessel in the template.

Figure 9:
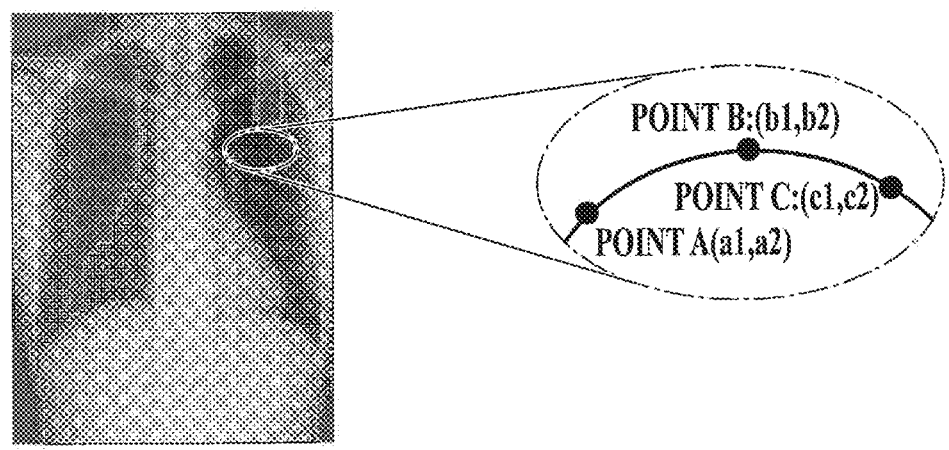
FIG. 9 is a schematic diagram illustrating three points for calculating a curvature of a pulmonary vessel.

With reference to FIG. 9, the curvature of the extracted pulmonary vessel can be determined by acquiring the coordinates of three points A, B, and C along the pulmonary vessel, calculating the radius (curvature radius) r of the circle from the simultaneous equations acquired by substituting the coordinates of the three points into the circle equation (refer to Expression 1), and calculating the inverse of the curvature radius r.

$$(x-x_0)^2+(y-y_0)^2=r^2 \qquad \text{Expression 1}$$

where $(x_0, y_0)$ indicates the coordinates of the origin of the circle and r indicates the radius of the circle.

(10) Variation in Vascular Diameter

Figure 10:
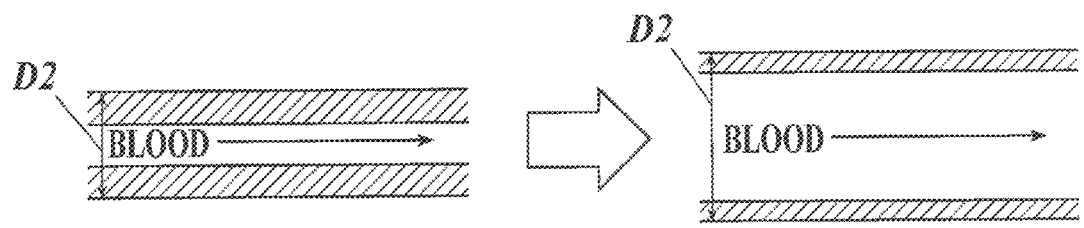
FIG. 10 illustrates variation in a cross section of the pulmonary vessel in response to a blood flow.

FIG. 10 illustrates variation in the cross section of a pulmonary vessel in response to the blood flow. With reference to FIG. 10, the blood flow into the pulmonary vessel expands the pulmonary vessel or extends its diameter.

In the first step of calculating the variation in vascular diameter, the pulmonary vessels are extracted from the lung field regions in respective frame images and then labeled. The vascular diameters of the respective extracted vessels are then calculated. The vascular diameter is determined by, for example, measuring the width D2 of the vessel region as illustrated in FIG. 10. The variation in vascular diameter is then determined by calculating the difference or ratio between the maximum and minimum vascular diameters among those of the corresponding vessels (provided with the identical labels) of the frame images.

(11) Rate of Variation in Density of the Pulmonary Vessels

The signal value (density value) of the lung field in a radioactive (x-ray) image varies in response to the blood flow in the pulmonary vessels caused by the heartbeat. As the blood flow increases, the density value in the image decreases. That is, a local variation in density of the lung field region is caused by variation in blood flow of the pulmonary vessels existing in a local region.

Figure 11:
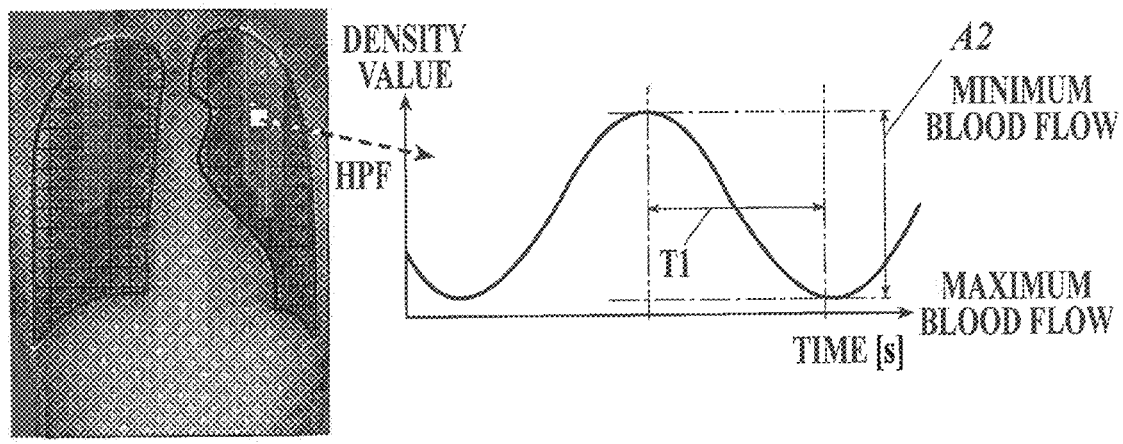
FIG. 11 is a schematic diagram illustrating a procedure of calculating a rate of variation in density of the pulmonary vessel.

FIG. 11 is a schematic diagram illustrating a procedure of calculating the rate of variation in density of the pulmonary vessels.

First, the variation in density of the pulmonary vessels is calculated. For example, the lung field region in each frame image is divided into subregions. The subregions are then correlated with the respective subregions in the other frame images. For each subregion, a representative value (e.g., an average or median value) of signal values (density values) of the pixels in the subregion is calculated. The calculated representative value is substituted for the signal values of the pixels in the subregion. The temporal variation in the substituted representative value is then subject to a high-pass filtering (HPF) process in the time domain. In a single respiratory cycle of the wave graph representing the temporal variation in signal value after the high-pass filtering process, the difference A2 of the maximum signal value (at the minimum blood flow) and the minimum signal value (at the maximum blood flow) is calculated as the variation in density of the pulmonary vessels. The high-pass filtering process in the time domain removes low-frequency variations in signal value caused by the ventilation from the dynamic image, to extract the temporal variation in signal value (temporal frequency components at high frequency) caused by the blood flow. For example, the temporal variation in signal value in each subregion is extracted with a filter having a cutoff frequency of 0.8 Hz. Although the high-pass filter is used to extract the temporal variation in signal value caused by the blood flow in this embodiment, a band-pass filter may be alternatively used to extract certain frequency components. An example band-pass filter has a low cutoff frequency of 0.8 Hz and a high cutoff frequency of 2.4 Hz.

Second, the rate of variation in density of the pulmonary vessels is calculated by dividing the variation in density of the pulmonary vessels by the blood inflow time. The blood inflow time indicates the time T1 (refer to FIG. 11) from the minimum to maximum blood flows (density values). In other words, the blood inflow time indicates the time from the maximum to minimum signal values in the wave graph representing the temporal variation in density after the high-pass filtering process.

(12) Rate of Variation in Vascular Diameter

The rate of variation in vascular diameter can be calculated by dividing the variation in vascular diameter by the vessel expansion time. The vessel expansion time indicates the time from the minimum to maximum vascular diameters.

(13) Rate of Variation in Density of a Pulmonary Vessel Between Two Sites

Figure 12:
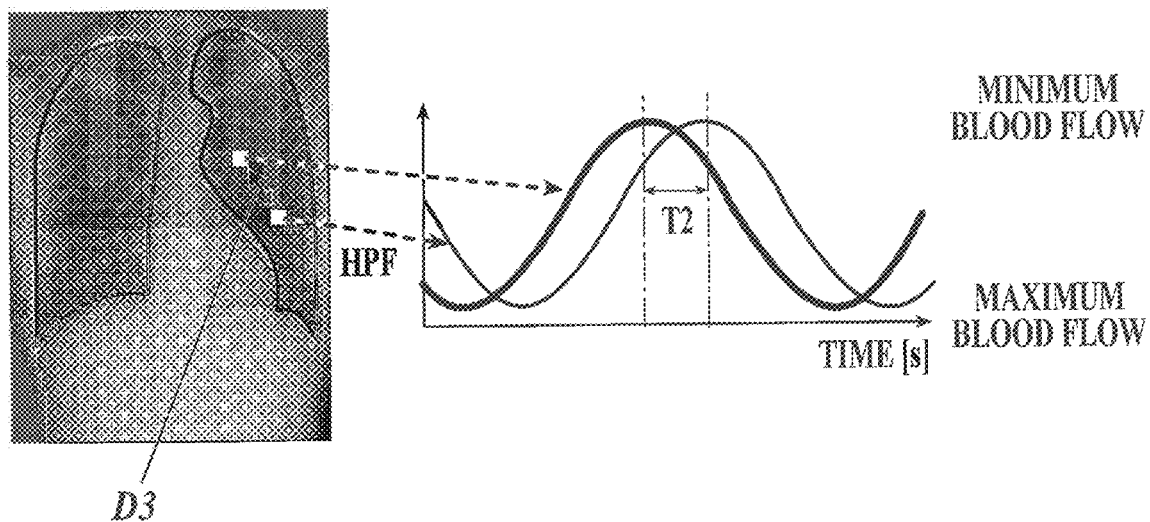
FIG. 12 is a schematic diagram illustrating a procedure of calculating a rate of variation in density of the pulmonary vessel between two sites.

The rate of variation in density of a pulmonary vessel between two sites is calculated by dividing the distance D3 (refer to FIG. 12) between these two sites in the lung field by the time lag T2. The time lag T2 indicates the difference in time between the minimum blood flow at one site and the minimum blood flow at the other site.

(14) Rate of Variation in Vascular Diameter Between Two Sites

The rate of variation in vascular diameter between two sites is calculated by dividing the distance between these two sites in the lung field by the time lag. The time lag indicates the difference in time between the start of expansion of the pulmonary vessel (having the minimum diameter) at one site and the start of expansion of the pulmonary vessel at the other site.

On the basis of the calculated index values representing variations in the pulmonary vessels, the flexibility of the pulmonary vessels is evaluated (Step S15).

In the case of the index value (9) or (10) calculated in Step S14, the control unit 31 acquires the reference range of index value, which corresponds to the test subject's physical characteristics (e.g., age, sex, and heart volume) added to the dynamic image or corresponds to the heart area calculated from the dynamic image, for example, from the storage unit 32. The control unit 31 then evaluates the flexibility of the pulmonary vessels based on comparison of the index value calculated in Step S14 with the acquired reference range.

In the case of the index value (9) or (10) calculated in Step S14, the pulmonary vessels are evaluated more flexible for a larger index value. For example, the pulmonary vessels are evaluated more flexible than normal for the index value calculated in Step S14 that exceeds the reference range. The pulmonary vessels are evaluated normal for the index value calculated in Step S14 that is within the reference range. The pulmonary vessels are evaluated less flexible than normal for the index value calculated in Step S14 that falls below the reference range. The control unit 31 also calculates the deviation of the index value calculated in Step S14 from the reference range as an evaluated value indicating the flexibility of the pulmonary vessels.

In the case of any one of the index values (11) to (14) calculated in Step S14, the control unit 31 acquires the reference range of index value, which corresponds to the information on the heart volume added to the dynamic image or corresponds to the heart area or heart rate calculated from the dynamic image, for example, from the storage unit 32. The control unit 31 then evaluates the flexibility of the pulmonary vessels based on comparison of the index value calculated in Step S14 with the acquired reference range. The pulmonary blood flow is caused by the heartbeat. The heart rate can thus be determined by acquiring the wave graph representing the variation in density of the lung field in response to the blood flow from the dynamic image, and acquiring the blood flow cycle from the wave graph. The heart area can be acquired by multiplying the pixel size by the number of pixels in the contour of the heart extracted from the dynamic image. The contour of the heart can be extracted by any known image processing technique, for example, the technique disclosed in Japanese Patent No. 2796381.

In the case of any one of the index values (11) to (14) calculated in Step S14, the pulmonary vessels are evaluated more flexible for a smaller index value (lower rate). For example, the pulmonary vessels are evaluated less flexible than normal for the index value calculated in Step S14 that exceeds the reference range. The pulmonary vessels are evaluated normal for the index value calculated in Step S14 that is within the reference range. The pulmonary vessels are evaluated more flexible than normal for the index value calculated in Step S14 that falls below the reference range. The control unit 31 also calculates the deviation of the index value calculated in Step S14 from the reference range as an evaluated value indicating the flexibility of the pulmonary vessels. A flexible blood vessel readily curves and thus has high resistance. That is, a more flexible pulmonary vessel provides a slower blood flow, slower variation in density of the pulmonary vessels, and slower variation in vascular diameter. In contrast, a hard blood vessel has an approximately straight shape and thus has low resistance. That is, a less flexible pulmonary vessel provides a more rapid blood flow, more rapid variation in density of the pulmonary vessels, and more rapid variation in vascular diameter.

The display unit 34 then displays an evaluation result screen indicating the results of evaluation (Step S16). The evaluation result screen displayed in Step S16 is not illustrated in any of the drawings but is equivalent to that illustrated in FIG. 8. For example, the evaluation result screen includes a color mapping display where the subregions have different colors corresponding to the evaluation results (more flexible than normal, normal, and less flexible than normal) on the reference image, and an evaluation value display where the evaluated values of the subregions are displayed with numeric values. The evaluation value display may always display the values of all the subregions, or may display only the value of the subregion designated on the image in the color mapping display by the operation unit 33 (clicked or pointed with the cursor).

As described above, the control unit 31 of the diagnostic console 3 calculates the index value representing variation in the lung field from the dynamic image of the breast, and evaluates the flexibility of the lung field based on the calculated index value. This configuration can evaluate the flexibility of the lung field from the dynamic image. The control unit 31 also calculates the index value representing variations in pulmonary vessels from the dynamic image of the breast, and evaluates the flexibility of the pulmonary vessels based on the calculated index value. This configuration can evaluate the flexibility of the pulmonary vessels from the dynamic image.

The illustrated embodiment is a mere example of preferable embodiments of the dynamic analysis system of the present invention and should not be construed to limit the present invention.

For example, although the flexibility of a target portion (lung field or pulmonary vessel) is evaluated based on comparison of the index value representing variation in the target portion calculated from the dynamic image with a reference value in the embodiment, the flexibility may be evaluated by any other procedure.

For example, the index values representing variations in the target portion may be calculated in multiple regions set in the dynamic image, and the calculated evaluation values of the regions are compared to evaluate the relative flexibilities of the target portions of the plural regions. In detail, the lung field is divided into multiple subregions as illustrated in FIG. 8, and the variations in density of the regions 1 and 3 in the lung field are then calculated. In this case, the calculated index values are compared between the regions 1 and 3. For example, in the case of the index value of the region 3 larger than the index value of the region 1, the region 3 is evaluated more flexible than the region 1. This configuration can compare the flexibility of the target portion between the multiple regions. This procedure of evaluation can be applied to an index value that can be calculated for each region. Examples of such an index value include variation in density of the lung field, the rate of variation in density of the lung field, the rate of variation in density of the pulmonary vessels, a variation in a vascular diameter, and the rate of variation in the vascular diameter.

Alternatively, the index values representing variations in the target portion may be calculated from multiple dynamic images (e.g., dynamic images taken in different times) of the identical subject (the identical target portion of the identical test subject), for example. In this case, the flexibilities of the target portion in the individual dynamic images are evaluated based on comparison between the calculated index values. For example, the index value representing variation in the lung field is calculated from each of the current dynamic image and the past dynamic image taken one month before of the breast. In this case, based on comparison between the calculated index values, the current lung field is evaluated more flexible than the lung field one month before, for example. This configuration allows a doctor to readily observe a temporal variation in flexibility of the target portion of the identical patient.

The evaluation based on comparison of the index value with the reference value, the evaluation based on comparison of the index values between regions, and the evaluation based on comparison of the index values between different dynamic images may be executed alone or appropriately combined with each other.

For example, although the flexibility of the target portion (lung field or pulmonary vessel) is evaluated from the breast dynamic image acquired by imaging the dynamic states of the breast of a human body in the embodiment, this example should not be construed to limit the present invention. The technique can also be applied to the evaluation of the flexibility of any other target portion based on a dynamic image of the portion.

For example, although the hard disk or nonvolatile semiconductor memory is used as a computer-readable medium for storing the programs of the present invention in the embodiment, this example should not be construed to limit the present invention. For example, the computer-readable medium may be any other portable recording medium (e.g., CD-ROM). In addition, the medium providing data on the programs of the present invention via a communication line may be carrier waves.

Any specific configuration or operation of each component of the dynamic analysis system 100 may be appropriately modified within the gist of the present invention.

What is claimed is:

1. A dynamic analysis system comprising:
a diagnostic console which calculates at least one index value representing variation in a target portion of a human body from at least one dynamic image acquired by performing radiographic imaging to a subject containing the target portion, and evaluates flexibility of the target portion based on the calculated index value,
wherein the dynamic image is a breast dynamic image, the target portion is a lung field, and the diagnostic console calculates the index value representing variation in the lung field from the breast dynamic image, and evaluates the flexibility of the lung field based on the calculated index value representing the variation in the lung field,
wherein the diagnostic console calculates from the dynamic image, as the index value representing the variation in the lung field, at least one of: a variation in area of the lung field, and a rate of variation in the area of the lung field,
wherein the diagnostic console includes a display unit that displays the dynamic image and displays an evaluation result of the flexibility of the lung field on the dynamic image; and
a storage device which stores a reference value of the index value in association with one or more of: height; weight; age; sex; respiratory strategy; volume of the lung field; area of the lung field; and respiratory rate, wherein
the diagnostic console evaluates the flexibility of the lung field based on comparison of the calculated index value with the reference value stored in the storage device, the reference value being associated with a test subject who becomes the subject of the dynamic image, and the diagnostic console evaluates the lung field more flexible for the lamer variation in the area of the lung field.

2. The dynamic analysis system of claim 1, wherein the diagnostic console extracts a signal of a certain temporal frequency component from the dynamic image, and calculates the variation in density of the lung field region and/or the rate of variation in density of the lung field region from the dynamic image from which the certain temporal frequency component is extracted.

3. The dynamic analysis system of claim 1, wherein the diagnostic console evaluates the lung field more flexible for the higher rate of variation in the area of the lung field.

4. The dynamic analysis system of claim 1, wherein the diagnostic console calculates from at least two regions set in a lung field region in the dynamic image, as further index values, a variation in density in each of the regions or a rate of variation in density in each of the regions, and evaluates the flexibility of the lung field based on comparison between the index values calculated from the at least two regions.

5. The dynamic analysis system of claim 1, wherein the diagnostic console calculates the index values each representing variation in the lung from the respective dynamic images acquired by imaging the identical subject at different times, and evaluates the flexibility of the lung field based on comparison between the calculated index values.

6. The dynamic analysis system of claim 1, wherein the diagnostic console calculates from the dynamic image, as a further index value representing the variation in the lung field, at least one of: a variation in density of a lung field region, a movement of a diaphragm, a movement of a periphery of a thorax, a rate of variation in density of the lung field region, a rate of variation in the area of the lung field, a rate of movement of the diaphragm, and a rate of movement of the periphery of the thorax.

7. The dynamic analysis system of claim 1, wherein the evaluation result displayed on the dynamic image indicates whether the lung field is more flexible or less flexible than a reference.

8. A dynamic analysis system comprising:
a diagnostic console which calculates at least one index value representing variation in a target portion of a human body from at least one dynamic image acquired by performing radiographic imaging to a subject containing the target portion, and evaluates flexibility of the target portion based on the calculated index value,
wherein the dynamic image is a breast dynamic image, the target portion is a pulmonary vessel, and the diagnostic console calculates the index value representing variation in the pulmonary vessel from the breast dynamic image, and evaluates the flexibility of the pulmonary vessel based on the calculated index value representing the variation in the pulmonary vessel, and
wherein the diagnostic console calculates from the dynamic image, as the index value representing the variation in the pulmonary vessel, at least one of: a rate of variation in density of the pulmonary vessel; a rate of variation in diameter of the pulmonary vessel; a rate of variation in density of the pulmonary vessel between two sites; and a rate of variation in diameter of the pulmonary vessel between two sites; and
a storage device which stores a reference value of the index value in association with one or more of: age; sex; heart volume; heart area; and heart rate, wherein
the diagnostic console evaluates the flexibility of the pulmonary vessel based on comparison of the calculated index value with the reference value stored in the storage device, the reference value being associated with a test subject who becomes the subject of the dynamic image.

9. The dynamic analysis system of claim 8, wherein the diagnostic console calculates, as a deformation of the pulmonary vessel, a variation in curvature of the pulmonary vessel between a contracted mode and an expanded mode.

10. The dynamic analysis system of claim 8, wherein the diagnostic console extracts a signal of a certain temporal frequency component from the dynamic image, and calculates the rate of variation in density of the pulmonary vessel and/or the rate of variation in density of the pulmonary vessel between two sites from the dynamic image from which the certain temporal frequency component is extracted.

11. The dynamic analysis system of claim 8, wherein the diagnostic console evaluates the pulmonary vessel more flexible for the larger deformation of the pulmonary vessel or the larger variation in diameter of the pulmonary vessel.

12. The dynamic analysis system of claim 8, wherein the diagnostic console evaluates the pulmonary vessel more flexible for the lower rate of variation in density of the pulmonary vessel, the lower rate of variation in diameter of the pulmonary vessel, the lower rate of variation in density of the pulmonary vessel between two sites, or the lower rate of variation in diameter of the pulmonary vessel between two sites.

13. The dynamic analysis system of claim 8, wherein the diagnostic console calculates from at least two regions set in a lung field region in the dynamic image, as the index values, a rate of variation in density of the pulmonary vessel in each of the regions, a variation in diameter of the pulmonary vessel in each of the regions, or a rate of variation in diameter of the pulmonary vessel in each of the regions, and evaluates the flexibility of the pulmonary vessel based on comparison between the index values calculated from the at least two regions.

14. The dynamic analysis system of claim 8, wherein the diagnostic console calculates the index values each representing variation in the pulmonary vessel from the respective dynamic images acquired by imaging the identical subject at different times, and evaluates the flexibility of the pulmonary vessel based on comparison between the calculated index values.

15. The dynamic analysis system of claim 8, wherein the diagnostic console includes a display unit that displays the dynamic image and displays an evaluation result of the flexibility of the pulmonary vessel on the dynamic image.

16. The dynamic analysis system of claim 15, wherein the evaluation result displayed on the dynamic image indicates whether the pulmonary vessel is more flexible or less flexible than a reference.

17. A dynamic analysis system comprising:
a diagnostic console which calculates at least one index value representing variation in a target portion of a human body from at least one dynamic image acquired by performing radiographic imaging to a subject containing the target portion, and evaluates flexibility of the target portion based on the calculated index value,
wherein the dynamic image is a breast dynamic image, the target portion is a lung field, and the diagnostic console calculates the index value representing variation in the lung field from the breast dynamic image, and evaluates the flexibility of the lung field based on the calculated index value representing the variation in the lung field,
wherein the diagnostic console calculates from the dynamic image, as the index value representing the variation in the lung field, at least one of: a variation in density of a lung field region, a variation in area of the lung field, a movement of a diaphragm, a movement of a periphery of a thorax, a rate of variation in density of the lung field region, a rate of variation in the area of the lung field, a rate of movement of the diaphragm, and a rate of movement of the periphery of the thorax,
wherein the diagnostic console includes a display unit that displays the dynamic image and displays an evaluation result of the flexibility of the lung field on the dynamic image, and
wherein the diagnostic console calculates the index values each representing variation in the lung from the respective dynamic images acquired by imaging the identical subject at different times, and evaluates the flexibility of the lung field based on comparison between the calculated index values.

18. A dynamic analysis system comprising:
a diagnostic console which calculates at least one index value representing variation in a target portion of a human body from at least one dynamic image acquired by performing radiographic imaging to a subject containing the target portion, and evaluates flexibility of the target portion based on the calculated index value,
wherein the dynamic image is a breast dynamic image, the target portion is a pulmonary vessel, and the diagnostic console calculates the index value representing variation in the pulmonary vessel from the breast dynamic image, and evaluates the flexibility of the pulmonary vessel based on the calculated index value representing the variation in the pulmonary vessel, and wherein the diagnostic console calculates from the dynamic image, as the index value representing the variation in the pulmonary vessel, at least one of: a rate of variation in density of the pulmonary vessel; a rate of variation in diameter of the pulmonary vessel; a rate of variation in density of the pulmonary vessel between two sites; and a rate of variation in diameter of the pulmonary vessel between two sites, and wherein the diagnostic console calculates from at least two regions set in a lung field region in the dynamic image, as the index values, a rate of variation in density of the pulmonary vessel in each of the regions, a variation in diameter of the pulmonary vessel in each of the regions, or a rate of variation in diameter of the pulmonary vessel in each of the regions, and evaluates the flexibility of the pulmonary vessel based on comparison between the index values calculated from the at least two regions.

19. A dynamic analysis system comprising:

a diagnostic console which calculates at least one index value representing variation in a target portion of a human body from at least one dynamic image acquired by performing radiographic imaging to a subject containing the target portion, and evaluates flexibility of the target portion based on the calculated index value, wherein the dynamic image is a breast dynamic image, the target portion is a lung field, and the diagnostic console calculates the index value representing variation in the lung field from the breast dynamic image, and evaluates the flexibility of the lung field based on the calculated index value representing the variation in the lung field, wherein the diagnostic console calculates from the dynamic image, as the index value representing the variation in the lung field, at least one of: a variation in area of the lung field, and a rate of variation in the area of the lung field, wherein the diagnostic console includes a display unit that displays the dynamic image and displays an evaluation result of the flexibility of the lung field on the dynamic image; and a storage device which stores a reference value of the index value in association with one or more of: height; weight; age; sex; respiratory strategy; volume of the lung field; area of the lung field; and respiratory rate, wherein the diagnostic console evaluates the flexibility of the lung field based on comparison of the calculated index value with the reference value stored in the storage device, the reference value being associated with a test subject who becomes the subject of the dynamic image, and the diagnostic console evaluates the lung field more flexible for the higher rate of variation in the area of the lung field.

* * * * *